United States Patent
Brown

(10) Patent No.: US 9,693,849 B2
(45) Date of Patent: Jul. 4, 2017

(54) HERNIA PATCH FRAME INCORPORATING BIO-ABSORBABLE MATERIAL

(71) Applicant: Roderick B. Brown, Glenwood, MN (US)

(72) Inventor: Roderick B. Brown, Glenwood, MN (US)

(*) Notice: Subject to any disclaimer, the term of this patent is extended or adjusted under 35 U.S.C. 154(b) by 379 days.

(21) Appl. No.: 14/631,103

(22) Filed: Feb. 25, 2015

(65) Prior Publication Data
US 2016/0242889 A1 Aug. 25, 2016

(51) Int. Cl.
*A61F 2/02* (2006.01)
*A61F 2/00* (2006.01)

(52) U.S. Cl.
CPC .... *A61F 2/0063* (2013.01); *A61F 2210/0004* (2013.01); *A61F 2210/0014* (2013.01); *A61F 2210/0019* (2013.01); *A61F 2220/005* (2013.01); *A61F 2220/0033* (2013.01); *A61F 2220/0058* (2013.01); *A61F 2220/0075* (2013.01)

(58) Field of Classification Search
CPC .......... A61F 2/0063; A61F 2002/0068; A61F 2210/0014; A61F 2210/0004; A61F 2210/0019; A61F 2220/0033; A61F 2220/0075; A61F 2220/0058; A61F 2220/005
See application file for complete search history.

(56) References Cited

U.S. PATENT DOCUMENTS

| | | |
|---|---|---|
| 5,824,082 A | 10/1998 | Brown |
| 9,173,731 B2 * | 11/2015 | Brown .................. A61F 2/0063 |
| 2007/0265710 A1 | 11/2007 | Brown et al. |
| 2010/0261956 A1 * | 10/2010 | Townsend ............. A61F 2/0045 600/37 |
| 2014/0058416 A1 * | 2/2014 | Brown .................. A61F 2/0063 606/151 |

* cited by examiner

*Primary Examiner* — Jonathan Miles
*Assistant Examiner* — Wade Miles
(74) *Attorney, Agent, or Firm* — Nikolai & Mersereau P.A.; Thomas J. Nikolai

(57) ABSTRACT

A hernia repair prosthesis comprises a segmented frame forming a closed loop where a first segment comprises a helical hollow tube and a second segment comprises a solid strand. Both segments are preferably a metal exhibiting shape memory properties and the two segments are assembled with end portions of the second segment inserted into the lumen at opposed end portions of the first segment with a clearance fit. At manufacture, a covering layer of a bio-absorbable polymer on the end portions of the second strand is sufficiently sized to create a temporary interference fit between the two segments to inhibit relative movement between them. The ability of the intercoupled segment to move relative to one another is restored upon degradation of the polymer due to exposure to body fluids following implantation of the prostheses. A prosthetic fabric is attached to the segmented frame.

21 Claims, 4 Drawing Sheets

HERNIA PATCH FRAME INCORPORATING BIO-ABSORBABLE MATERIAL

CROSS-REFERENCED TO RELATED APPLICATIONS

Not applicable.

STATEMENT OF GOVERNMENT INTEREST

Not applicable.

BACKGROUND OF THE INVENTION

Field of the Invention

This invention relates generally to a prosthesis for the repair of hernias, and more particularly to an improved hernia repair patch, deliverable in a rolled form through a trocar in an endoscopic procedure and which deploys, when unconstrained, to a somewhat planar configuration.

Discussion of the Prior Art

In U.S. Pat. No. 5,824,082, I disclose a hernia repair patch comprising a single strand, closed loop, wire frame made of a shape memory alloy on which is attached a prosthetic mesh. That device was intended for deployment through a trocar in the course of an endoscopic hernia repair procedure. It was found that this prosthesis was somewhat difficult to deliver through a trocar of a sufficiently small diameter felt appropriate for use in typical endoscopic hernia repair surgery.

I later learned that a multifilar cable of Nitinol® strands as the frame allowed a more compact device when rolled for insertion, via a cannula, and this improvement is disclosed in published Application US 2007/0265710 A1.

In very few cases, upon patient follow-up, x-rays revealed instances where strands comprising the cable frame had broken, but without any harm whatsoever to the patients. It has been theorized that the breakage may have been as result of fatigue due to stresses on the frame induced by body motion and flexures following the complete integration of the hernia patch into the surrounding tissue by normal tissue in-growth. Even though the observed instances of frame breakage have been small and have not resulted in any adverse patient outcomes, to alleviate any potential concern by surgeons, patients or regulatory authorities, I have now conceived of a solution that should avoid stress-induced fractures in hernia patch frames.

SUMMARY OF THE INVENTION

In accordance with the present invention, a hernia repair prosthesis comprises a segmented frame supporting a prosthetic mesh fabric, the frame forming a closed loop where first segments of the frame comprise helical, hollow, tubular metal strands and second segments comprise solid metal strands. In forming the frame, end portions of the second segments are inserted into end portions of the first segments and are dimensioned to be slidable therein. However, a bio-absorbable polymer is initially provided between the end portions of the second segments on the internal wall defining the tubular lumen of the first segments to create an interference fit that inhibits sliding. A prosthetic fabric is attached to the segmented frame. Following surgical implant and degradation of the polymer by body fluids at a time following stabilization of the hernia repair patch through tissue ingrowth through the mesh, the segments become free to move relative to one another and any stresses that might have been otherwise created in the frame are resolved in that the frame segments are permitted to move telescopically with respect to one another so that flexure of the frame at what would otherwise be a stress point is avoided.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
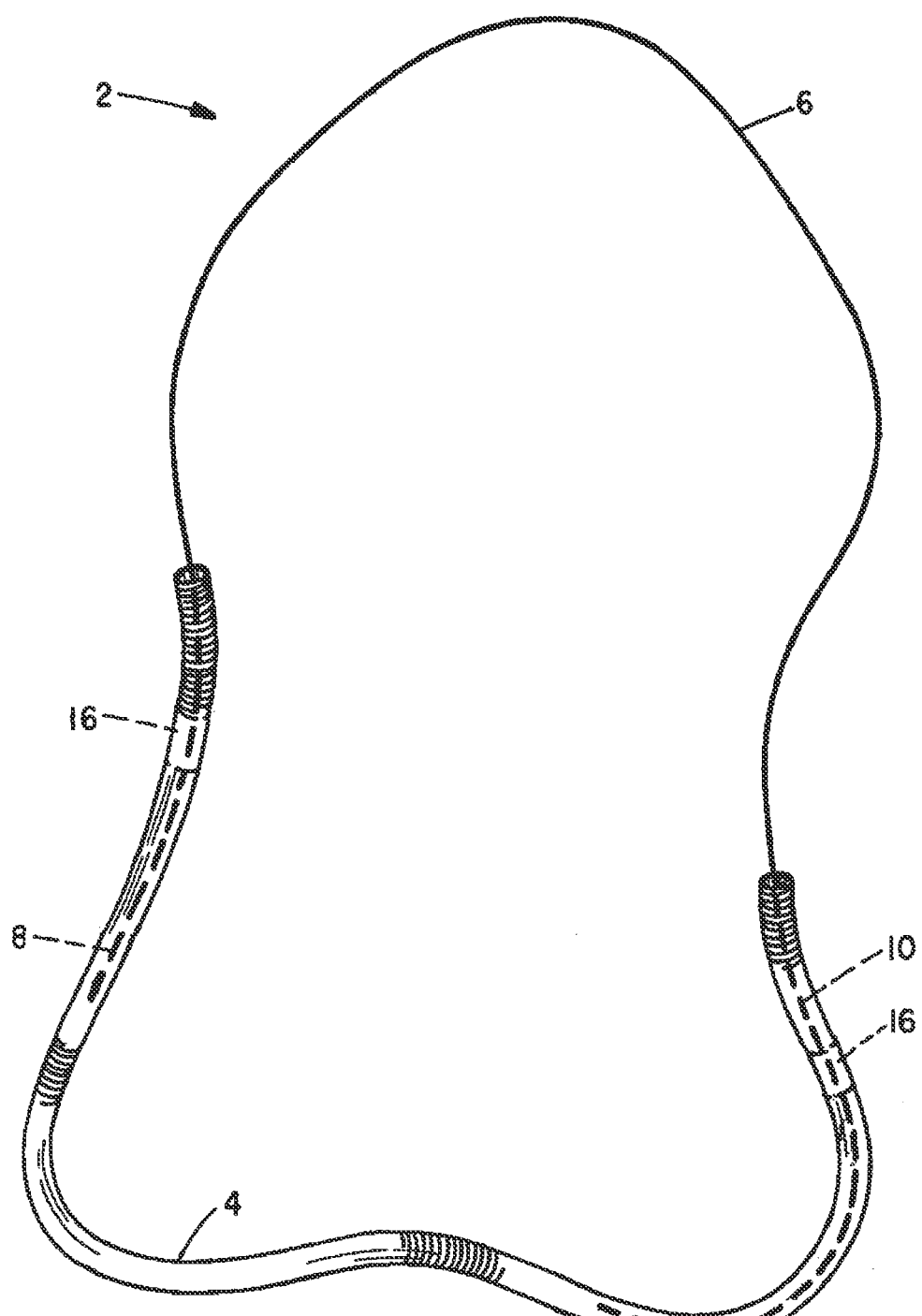
FIG. 1 is a perspective view of a frame of one embodiment of a hernia repair prosthesis constructed in accordance with the present invention.

This description of the preferred embodiments is intended to be read in connection with the accompanying drawings, which are to be considered part of the entire written description of this invention. In the description, relative terms such as "lower", "upper", "horizontal", "vertical", "above", "below", "up", "down", "top" and "bottom" as well as derivatives thereof (e.g., "horizontally", "downwardly", "upwardly", etc.) should be construed to refer to the orientation as then described or as shown in the drawings under discussion. These relative terms are for convenience of description and do not require that the apparatus be constructed or operated in a particular orientation. Terms such as "connected", "connecting", "attached", "attaching", "join" and "joining" are used interchangeably and refer to one structure or surface being secured to another structure or surface or integrally fabricated in one piece, unless expressively described otherwise.

In FIG. 1 the frame portion of a hernia repair prosthesis is indicated generally by numeral 2 and is seen to comprise a segmented frame forming a closed loop where a first segment 4 comprises a helical hollow tubular metal strand and a second segment 6 comprises a solid metal strand. The segment 4 is preferably of a type manufactured and sold by Fort Wayne Metals Inc. of Fort Wayne, Ind., and sold under the trademark, HHS®, an acronym for helical hollow strand.

Figure 3:
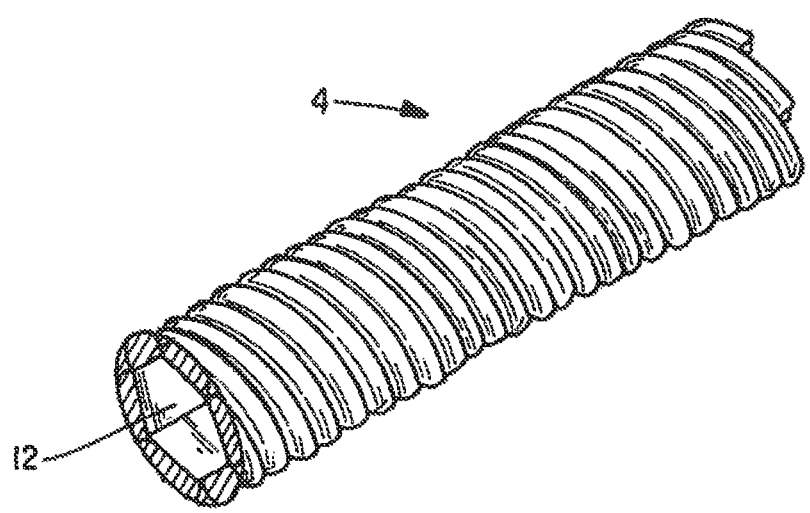
FIG. 3 is a perspective drawing showing a portion of the frame comprising a helical, hollow, tubular metal strand.

FIG. 3 is a perspective view of the HHS tubing that comprises six filars arranged in a single layer and, for the present application, the filars are preferably a nickel titanium alloy exhibiting shape memory properties. A suitable hernia patch may employ a Nitinol® strand 4 like that illustrated in FIG. 3 where the outer diameter may be in a range from 0.0025 inch to 0.25 inch while the strand 6 which may be a solid Nitinol wire or a cable formed from multiple filars and having an outside diameter in a range from 0.0024 inch to 0.24 inch. In forming the frame 2, the segments 4 and 6 may be heat-set in a suitable mold so as to exhibit a desired shape configuration in the manner more fully explained in the aforementioned published application US 2007/02365710 A1. The alloy is preferably such that the Nitinol used exhibits a transformation temperature at close to body temperature (37° C.).

With continued reference to FIG. 1, opposed end portions 8 and 10 of the second segment 6 are shown inserted into the lumen 12 (FIG. 3) of the first segment 4. The tolerances are such between the outer diameter of the solid strand 6 and the inner diameter of the helical hollow strand 4 such that there is sufficient clearance permitting the two segments to slide relative to one another. However, in accordance with the present invention, the end portions 8 and 10 of the segments 6 may be coated or otherwise provided with a layer 16 of a bio-absorbable polymer such as polyglycolic acid (PGA), polydioxanone or polylactic acid (PLA) or other bio-absorbable materials with similar properties which are formulated to become absorbed due to exposure to body fluids after a time sufficient to allow tissue ingrowth through the mesh to stabilize the prosthesis, e.g., two to twenty-four weeks. The polymer layer 16 is of a thickness to create one interference fit between end portions 8 and 10 of segment 6 and the inner wall of the segment 4 to temporarily prevent relative motion therebetween. Rather than applying a coating of bio-absorbable material to end portions of the wire or cable 6, the same effect can be achieved by inserting a bio-absorbable suture of an appropriate gauge to create an interference fit between the segments 4 and 6.

Figure 2:
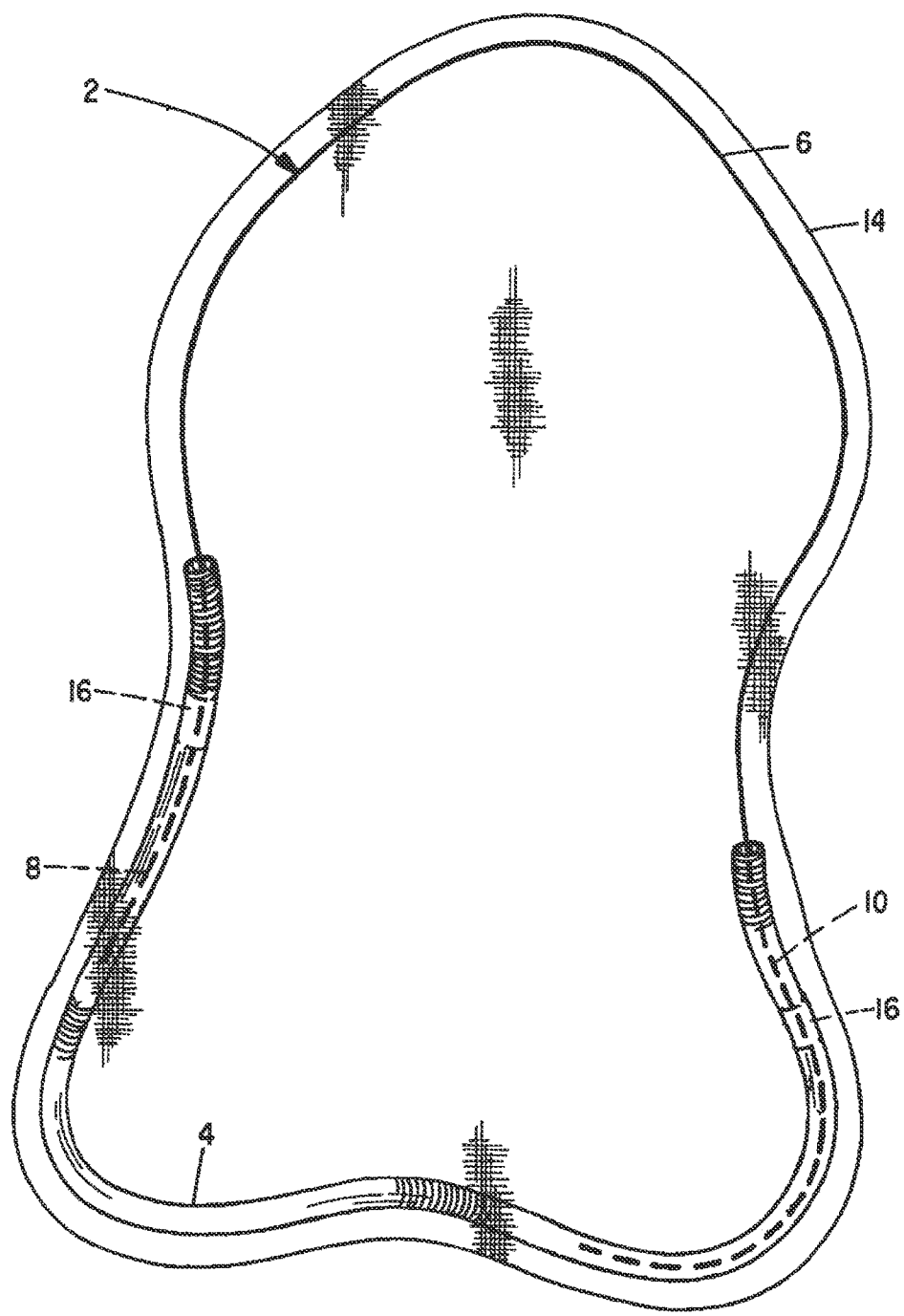
FIG. 2 is a view like that of FIG. 1 but with a prosthetic fabric attached to the frame.

FIG. 2 shows the frame 2 in assembled form as shown in FIG. 1 and with a prosthetic fabric 14 attached to the segmented frame 2. The prosthetic fabric is preferably a woven or a non-woven mesh of polypropylene, but also may be an expanded polytetrafluorethylene material, a polyester or any other approved fabric or biological material suitable for hernia and soft tissue repair. The fabric may be affixed to the frame 2 by stitching, or alternatively by thermal bonding, adhesive bonding or ultrasonic bonding.

From what has been described, those skilled in the art can appreciate that when the hernia patch of FIG. 2 is delivered into the abdominal cavity in a rolled form and allowed to expand and used to repair either a ventral hernia or an inguinal hernia, within a matter of several weeks from surgical placement in an endoscopic procedure, tissue ingrowth through the mesh results in incorporation of the hernia patch into surrounding muscle and fascial tissue at the repair site. Because the coupled segments 4 and 6 comprising the frame 2 are able to slide relative to one another upon bio-absorption of the polymer material 16 applied at the time of manufacture, any stress that might otherwise be imposed that might result ultimately in fatigue failure of one or more strands of the segment 6 is relieved due to the yielding action allowed by the frame construction of the present invention.

Figure 4:
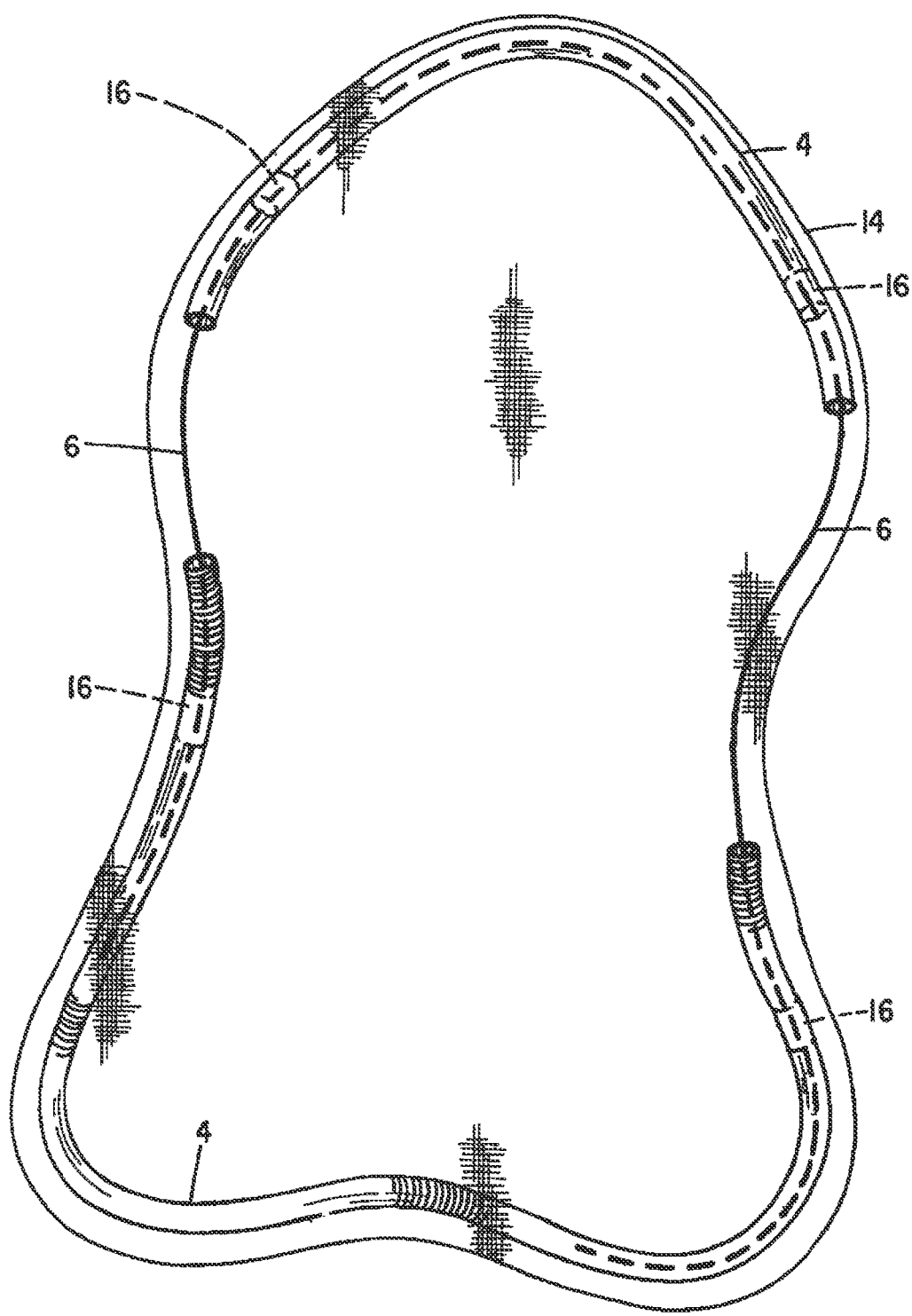
FIG. 4 is a perspective view of a second embodiment of the invention.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself. For example, instead of using HHS tubing, the strand 4 may comprise thin, solid wall tubing of a shape memory alloy. Likewise, the strand 6 may be a single wire, a multi-strand cable or a hollow tube of a lesser diameter than the I.D. of the tubular strand 4 that is employed. Also, while FIGS. 1 and 2 illustrate a two-member frame, it is also contemplated that the frame can be further segmented by using multiple strands like 4 and 6 coupled to one another in the manner shown in FIG. 4 with end portions of the strand 6 inserted into the lumens of intermediately positioned strands 4.

What is claimed is:

1. A hernia repair prosthesis comprising:
   (a) a segmented frame forming a closed loop where a first segment comprises an elongate tubular metal strand defining a lumen and a second segment comprises a solid metal strand with opposed end portions of the second segment inserted into opposed end portions of the first segment and slidable therein;
   (b) a bio-absorbable material disposed in the lumen of the first segment for temporarily inhibiting sliding motion between the first and second segments; and
   (c) a prosthetic fabric attached to the segmented frame.

2. The hernia repair prosthesis of claim 1 wherein the first and second segments comprise a shape memory alloy.

3. The hernia repair prosthesis of claim 2 wherein the second segment comprises plural strands twisted as a cable.

4. The hernia repair prosthesis of claim 2 wherein the shape memory alloy exhibits a transformation temperature of about 37° C.

5. The hernia repair prosthesis of claim 1 wherein the opposed ends of the second segment fit within the opposed ends of the first segment with a predetermined clearance fit upon absorption of the bio-absorbable material.

6. The hernia repair prosthesis of claim 1 wherein the prosthetic fabric is selected from a group consisting of a woven or a non-woven mesh of polypropylene and expanded polytetrafluorethylene.

7. The hernia repair prosthesis of claim 1 wherein the prosthetic fabric is affixed to the segmented frame by one of stitching, thermal bonding, adhesive bonding and ultrasonic bonding.

8. The hernia repair prosthesis of claim 1 wherein the helical hollow tubular metal strand has an outer diameter in a range of from 0.00025 inch to 0.0125 inch and an inner diameter in a range of from 0.0015 inch to 0.0110 inch.

9. The hernia repair prosthesis of claim 8 wherein the solid metal strand has an outer diameter in a range of from 0.0010 inch to 0.0095 inch.

10. The hernia repair prosthesis of claim 1 wherein the bio-absorbable material is a polymer selected from a group consisting of polyglycolic acid (PGA), polydioxanone, and polylactic acid (PLA).

11. A hernia repair prosthesis comprising:
    (a) segmented frame including a plurality of first segments and a plurality of second segments, each of the first segments comprising a metal strand wound as a helix and forming an elongate tube with a lumen, each of the second segments comprising a metal strand with opposed end portions, the second segments each being arranged with a first end portion thereof inserted into the lumen of one of said plurality of first segments and a second end portion thereof inserted into the lumen of another of said plurality of first segments to form a closed loop;
    (b) a bio-absorbable polymer disposed in the lumens for creating a temporary friction fit between end portions of the second segments and walls of the first segments defining said lumens; and
    (c) a prosthetic mesh fabric attached to the segmented frame.

12. The hernia repair prosthesis of claim 11 wherein the first and second segments comprise a shape memory alloy.

13. The hernia repair prosthesis of claim 12 wherein the second segments comprise plural strands twisted as a cable.

14. The hernia repair prosthesis of claim 12 wherein the shape memory alloy exhibits a transformation temperature of about 37° C.

15. The hernia repair prosthesis of claim 11 wherein the opposed ends of the second segments fit within the opposed ends of the first segments with a predetermined clearance fit upon absorption of the bio-absorbable material.

16. The hernia repair prosthesis of claim 11 wherein the prosthetic fabric is selected from a group consisting of a woven or a non-woven mesh of polypropylene and expanded polytetrafluorethylene.

17. The hernia repair prosthesis of claim 11 wherein the prosthetic fabric is affixed to the segmented frame by one of stitching, thermal bonding, adhesive bonding and ultrasonic bonding.

18. The hernia repair prosthesis of claim 11 wherein the elongate tube has an outer diameter in a range of from 0.0025 inch to 0.0125 inch and an inner diameter in a range of from 0.0015 inch to 0.0110 inch.

19. The hernia repair prosthesis of claim 18 wherein the solid metal strand has an outer diameter in a range of from 0.0010 inch to 0.0095 inch.

20. The hernia repair prosthesis of claim 11 wherein the bio-absorbable material is a polymer selected from a group consisting of polyglycolic acid (PGA), polydioxanone, and polylactic acid (PLA).

21. The hernia repair prosthesis of claim 11 wherein the bio-absorbable materials degradation time is in a range of from two to twenty-four weeks following exposure to body fluids.

* * * * *